(12) United States Patent
McDaniel

(10) Patent No.: US 6,388,099 B2
(45) Date of Patent: May 14, 2002

(54) PRODUCTION OF 8,8A-DIHYDROXY-6-DEOXYERYTHRONOLIDE B

(75) Inventor: Robert McDaniel, Palo Alto, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 0 days.

(21) Appl. No.: 09/768,927

(22) Filed: Jan. 23, 2001

Related U.S. Application Data

(63) Continuation-in-part of application No. 09/428,517, filed on Oct. 28, 1999, now Pat. No. 6,251,636.
(60) Provisional application No. 60/177,660, filed on Jan. 27, 2000, provisional application No. 60/120,254, filed on Feb. 16, 1999, and provisional application No. 60/106,100, filed on Oct. 29, 1998.

(51) Int. Cl.[7] ............................................. C07D 493/00
(52) U.S. Cl. ...................................................... 549/264
(58) Field of Search .......................................... 549/264

(56) References Cited

PUBLICATIONS

Shah, S. et al 'Cloning, characterization and heterologous expression of a polyketide synthase and P–450 oxidase involved in the biosynthesis of the antibiotic oleandomycin' CA 133:291766 (2000).*

Patterson, I. et al 'Degradation of oleandomycin: controlled removal of sugars to give oleandonolide C–3, C–5–acetonide' CA 109:129535 (1988).*

* cited by examiner

*Primary Examiner*—Amelia Owens
(74) *Attorney, Agent, or Firm*—Kevin Kaster; Carolyn A. Favorito

(57) ABSTRACT

The heterologous expression of the OlePKS in *Streptomyces lividans*, produces 8,8a-deoxyoleandolide, an aglycone precursor of oleandomycin. The co-expression with DEBS in *S. lividans* of the P450 monooxygenase OleP produces 8,8a-dihydroxy-6-deoxyerythonolide B and other derivatives that are precursors to important macrolide antibiotics.

15 Claims, 2 Drawing Sheets

Production of Oleandomycin

Production of 8,8a-dihydroxy-6-deoxyerythronolide B

PRODUCTION OF 8,8A-DIHYDROXY-6-DEOXYERYTHRONOLIDE B

CROSS-REFERENCE TO RELATED APPLICATIONS

This application claims priority to PCT patent application No. 99/24478, filed Oct. 22, 1999; and is a continuation-in-part of U.S. patent application Ser. No. 09/428,517, filed Oct. 28, 1999; now U.S. Pat. No. 6,251,636 which issued on Jun. 26, 2001; and claims priority to U.S. provisional application Ser. Nos. 60/177,660, filed Jan. 27, 2000, 60/120,254, filed Feb. 16, 1999, and 60/106,100, filed Oct. 29, 1998; each of which is incorporated herein by reference.

FIELD OF THE INVENTION

The present invention provides recombinant methods and materials for producing polyketides by recombinant DNA technology. The invention relates to the fields of agriculture, animal husbandry, chemistry, medicinal chemistry, medicine, molecular biology, pharmacology, and veterinary technology.

BACKGROUND OF THE INVENTION

Oleandomycin (compound (1) of FIG. 1) is a member of the macrolide class of antibiotics. Macrolides are a large family of polyketide natural products which include erythromycin, spiramycin, FK506, and avermectin (see Katz et al., *Polyketide synthesis: Prospects for hybrid antibiotics, Ann. Rev. Microbiol.* 47: 875–912, 1993; and Hopwood, *Genetic contributions to understanding polyketide synthases, Chem. Rev.* 97: 2465–2497,1997, each of which is incorporated herein by reference). The macrolactone core of oleandomycin, 8,8a-deoxyoleandolide (compound (2) of FIG. 1), like those of other macrolides, is synthesized by a modular polyketide synthase (PKS; see FIG. 1 and Swan et al., *Characterisation of a Streptomyces antibioticus gene encoding a type I polyketide synthase which has an unusual coding sequence, Molec. Gen. Genet.* 242: 358–362, 1994, and U.S. patent application Ser. No. 09/428,517, filed Oct. 28, 1999, now U.S. Pat. No. 6,251,636 which issued on Jun. 26, 2001, each of which is incorporated herein by reference). 8,8a-deoxyoleandolide is structurally identical to the macrolactone precursor of erythromycin, 6-deoxyerythronolide B (6-dEB, see compound (3) of FIG. 2), with the exception of a C-13 methyl instead of the C-13 ethyl group of 6-dEB. Thus, 6-dEB is derived from condensations between a propionate starter unit and six methylmalonate extender units, and 8,8a-deoxyoleandolide has an acetate starter unit.

The study of oleandomycin biosynthesis has been progressive over the past decade, due largely to the identification and sequencing of several biosynthetic and related genes by Salas and coworkers. Analysis of these gene sequences has revealed enzymes putatively involved in synthesis and attachment of the two deoxysugars, regulatory and antibiotic resistance genes, and a P-450 monooxygenase (see Rodriguez et al., *A cytochrome P450-like gene possibly involved in oleandomycin biosynthesis by Streptomyces antibioticus, FEMS Microbiol. Lett.* 127: 117–120, 1995; Olano et al., *Analysis of a Streptomyces antibioticus chromosomal region involved in oleandomycin biosynthesis, which encodes two glycosyltransferases responsible for glycosylation of the macrolactone ring, Mol. Gen. Genet.* 259: 299–308, 1998; and Quiros et al., *Two glycosyltransferases and a glycosidase are involved in oleandomycin modification during its biosynthesis by Streptomyces antibioticus, Mol. Microbiol.* 28: 1177–85, 1998, each of which is incorporated herein by reference). Thus, a single open reading frame (ORF) encoding a polypeptide subunit of a type I polyketide synthase was identified and, based on comparison to 6-deoxyerythronolide B synthase (DEBS), was hypothesized to encode the last two modules of the oleandomycin PKS (OlePKS; see Swan et al., supra). The cloning, characterization, and sequence determination of the other genes encoding the proteins of the OlePKS are described in PCT patent publication No. 00/026,349, incorporated herein by reference.

There remains, however, a need for additional methods and reagents to produce 8,8a-deoxyoleandolide, oleandomycin, and related compounds in heterologous host cells. The present invention meets these and other needs.

SUMMARY OF THE INVENTION

The gene cluster encoding the deoxyoleandolide polyketide synthase (OlePKS) was isolated from the oleandomycin producing strain *Streptomyces antibioticus*. Sequencing of the first two genes encoding OlePKS, together with the previously identified third gene revealed an overall genetic and protein architecture similar to that of the erythromycin gene cluster encoding the 6- deoxyerthronolide B synthase (DEBS) from *Saccharopolyspora erythraea*. When the entire OlePKS (10,487 amino acids) was expressed in the heterologous host *Streptomyces lividans*, it produced 8,8a-deoxyoleandolide (compound (2) of FIG. 1), the aglycone precursor of oleandomycin. The P450 monooxygenase, OleP, involved in oleandomycin biosynthesis was co-expressed with DEBS in *S. lividans*. The production of 8,8a-dihydroxy-6-deoxyerythonolide B (compound (6) of FIG. 2) and other derivatives demonstrates that OleP is involved in the epoxidation pathway of oleandomycin biosynthesis. Further, a method of producing 8,8a-dihydroxy-6-deoxyerythonolide B or 8,8a-dihydroxyoleandolide comprising the heterologous expression of DEBS or Ole PKS, respectively, with OleP in *S. lividans* was developed. This heterologous expression system provides a means to produce these compounds, which can directly or after further modification be hydroxylated and glycosylated to provide useful macrolide antibiotics.

Thus, in one embodiment, the present invention provides a method for introducing one or more hydroxyl groups or an epoxide into a polyketide, which method comprises expressing a recombinant gene encoding a P450 monooxygenase in a host cell. In one embodiment, the P450 monooxygenase is not naturally expressed by the host cell. In another embodiment, neither the P450 monooxygenase nor the polyketide is naturally expressed by the host cell. In a preferred embodiment, the host cell is a Streptomyces host cell. In another preferred embodiment, the P450 monooxygenase is OleP. In another preferred embodiment, the polyketide synthase is 6-deoxyerythronolide B synthase or 8,8a-deoxyoleandolide synthase.

DETAILED DESCRIPTION OF THE INVENTION

Figure 1:
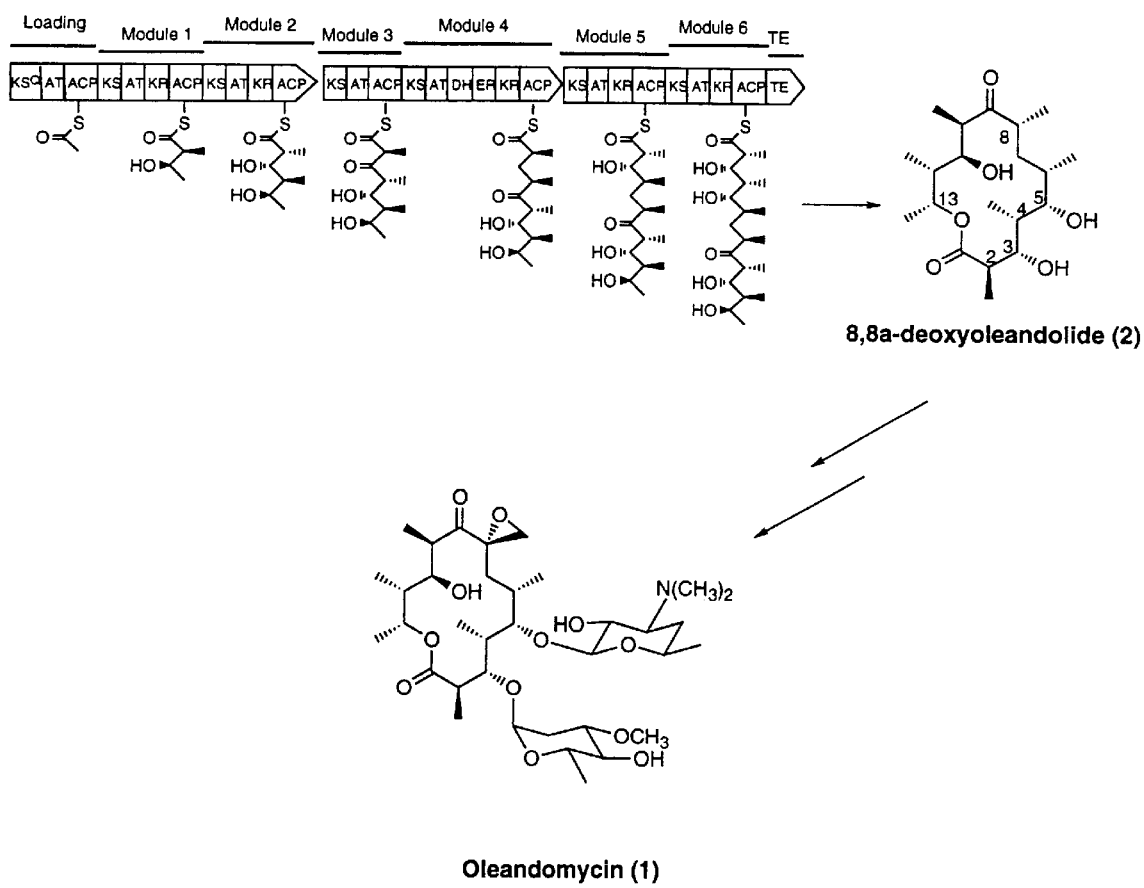
FIG. 1 shows a schematic for the biosynthesis of 8,8a-deoxyoleandolide (compound (2)), the macrolactone precursor of oleandomycin (compound (1)). The oleandomycin PKS consists of six modules, a loading domain, and a thioesterase (TE) on three separate polypeptides. In the Figure, the following abbreviations are used: KS, ketosynthase; AT, acytransferase; KR, ketoreductase; DH, dehydratase, ER, enoylreductase; ACP, acyl carrier protein; $KS^Q$, a KS-like domain that contains instead of an active-site cysteine a glutamine.

The present invention relates to the heterologous expression of the OlePKS coding sequence and/or OleP, the P-450 hydroxylase that converts 8,8a-deoxyoleandolide to oleandolide in *Streptomyces antibioticus*. The OlePKS is encoded by three ORFs—oleAI, oleAII, and the previously identified ORFB (see Swan et al., supra; ORFB is designated oleAII)—that span 35 kb of DNA. Each of the ORFs encodes two PKS modules, as in eryAI-AIII, and examination of the active site domains within the modules also reveals an organization similar to the active site arrangement of DEBS, as shown in Table 1, below. The sequence of the OlePKS genes and recombinant vectors from which those genes can be isolated are described in PCT publication No. 00/026349, incorporated herein by reference.

TABLE 1

Functions of oleandomycin PKS domains

| ORF | Amino acids | Deduced function | | | | | |
|---|---|---|---|---|---|---|---|
| OleAI | 4151 | | | | | | |
| Loading | 1025 | $KS^Q$ | AT | ACP | | | |
| Module 1 | 1465 | KS | AT | KR | ACP | | |
| Module 2 | 1520 | KS | AT | KR | ACP | | |
| OleAII | 3817 | | | | | | |
| Module 3 | 1543 | KS | AT | KR | ACP | | |
| Module 4 | 2117 | KS | AT | DH | ER | KR | ACP |
| OleAIII | 3520 | | | | | | |
| Module 5 | 1531 | KS | AT | KR | ACP | | |
| Module 6 | 1532 | KS | AT | KR | ACP | TE | |

The similarity observed between the OlePKS and DEBS was not unexpected given the structural relationship of the polyketides produced by the enzymes encoded by the two gene clusters. Yet the amino acid sequences (45% aa identity) of OlePKS and DEBS are surprisingly different from one another. A significant departure was found in the OlePKS loading domain.

In contrast with the loading module of DEBS, which consists of an acyl transferase (AT) domain—that loads a propionate starter unit—and an acyl carrier protein (ACP), the OlePKS loading module has an additional KS-like domain ($KS^Q$) with a glutamine instead of a cysteine at the active site. These domains have been shown to decarboxylate acylthioesters within PKSs and the related fatty acid synthases (see Witkowski et al., *Conversion of β3-ketoacyl synthase to a malonyl decarboxylase by replacement of the active-site cysteine with glutamine*, Biochemistry, 1999; and Bisang et al., *A chain initiation factor common to both modular and aromatic polyketide synthases*, Nature 401: 502–505, 1999, each of which is incorporated herein by reference). Therefore, the OlePKS is believed to initiate 8,8a-deoxyoleandolide synthesis by loading the ACP with a malonate unit and performing a decarboxylation to generate acetyl-ACP.

The heterologous production of 8,8a-deoxyoleandolide can be accomplished in *Streptomyces lividans* and *S. coelicolor*. Preferred strains of these organisms are described in U.S. Pat. No. 5,672,491 and U.S. patent application Ser. No. 09/181,833, filed Oct. 28, 1998, incorporated herein by reference. A vector for heterologous expression of the OlePKS was constructed in a manner analogous to those developed for DEBS and the picromycin PKS (PicPKS; see Kao et al., *Engineered biosynthesis of a complete macrolactone in a heterologous host*, Science 265: 509–512, 1994; Tang et al., *Elucidating the mechanism of chain termination switching in the picromycin/methymycin polyketide synthase*, Chem. & Biol. 6: 553–558, 1999; and PCT publication No. 99/61599, each of which is incorporated herein by reference). Plasmid pKOS098-4 is an autonomously replicating SCP2*-based shuttle vector containing the three OlePKS open reading frames downstream of the *S. coelicolor* actI promoter and actII-ORF4 transcriptional activator.

Transformation of *Streptomyces lividans* K4-155 with this vector resulted in a strain that produced ~50 mg/L of compound (2) of FIG. 1, confirming that 8,8a-deoxyoleandolide is the biosynthetic intermediate produced by the oleandomycin PKS. The mass spectrum and LC retention time of compound (2) of FIG. 1 were identical to known standards. The amount of 8,8a-deoxyoleandolide produced is similar to production levels of 6-dEB and narbonolide achieved with DEBS and PicPKS, respectively, using the same host and vector (Kao et al., Science 265: 509–512, 1994; and Tang et al., Chem. & Biol. 6: 553–558, 1999, each of which is incorporated herein by reference).

The invention further provides a method of producing mono and dihydroxy derivatives of 6-deoxyerythronolide B and 8,8a-deoxyoleandolide in recombinant host cells. In one embodiment, the 6-dEB compound is produced by recombinant expression of a 6-dEB synthase, such as that produced by the eryA or meg genes (the meg genes are described in PCT patent application US00/27433, incorporated herein by reference). In another embodiment, 8,8a-deoxyoleandolide is produced by recombinant expression of the OlePKS.

For example, 8,8a-dihydroxy-6-deoxyerythonolide B can be produced by the heterologous expression of DEBS with OleP in a Streptomyces host cell, such as *S. lividans*. The oleP gene is located approximately 6 kb downstream of the end of oleAIII (see Rodriguez et al., *A cytochrome P450-like gene possibly involved in oleandomycin biosynthesis by Streptomyces antibioticus.*, FEMS Microbiol. Lett. 127: 117–120, 1995, incorporated herein by reference). This gene encodes a cytochrome P450 monooxygenase homologous to several macrolide oxidases such as those found in the erythromycin (Weber et al., *An erythromycin derivative produced by targeted gene disruption in Saccharopolyspora erythraea.*, Science 252: 114–117, 1991; Haydock et al., *Cloning and sequence analysis of the genes involved in erythromycin biosynthesis in Saccharopolyspora erythraea; sequence similarities between eryG and a family of S-adenosylmethionine-dependent methyltransferases.*, Mol. Gen. Genet. 230: 120–128, 1991; and Stassi et al., *Identification of a Saccharopolyspora erythraea gene required for the final hydroxylation step in erythromycin biosynthesis.*, J. Bacteriol. 175: 182–189, 1993, each of which is incorporated herein by reference), picromycin/methymicin (Betlach et al., *Characterization of the macrolide P-450 hydroxylase from Streptomyces venezuelae which converts narbomycin to picromycin.*, Biochemistry 37: 14937–14942, 1998; and Xue et al., *Hydroxylation of macrolactones YC-17 and narbomycin is mediated by the pikC-encoded cytochrome P450 in Streptomyces venezuelae.*, Chem. & Biol. 5: 661–667, 1998, each of which is incorporated herein by reference), and tylosin gene clusters (Merson-Davies et al., *Analysis of five tylosin biosynthetic genes from the tylIBA* region of the *Streptomyces fradiae* genome., *Mol. Microbiol.* 13: 349–355, 1994, incorporated herein by reference).

Although the gene product OleP is putatively involved in formation of the oleandomycin epoxide moiety, several experiments have failed to establish its role (Rodriguez et al., *FEMS Microbiol. Lett.* 127: 117–120, 1995, incorporated herein by reference). Furthermore, the biochemical mechanism of epoxidation is not known and, therefore, whether any other enzymes are required in addition to OleP is also not known. When the epoxidation step occurs during biosynthesis is also not understood (see Spagnoli et al., *Biological conversion of erythronolide B, an intermediate of erythromycin biogenisis, into new "hybrid" macrolide antibiotics, J. Antibiotics* 36: 365–375, 1983, and Tatsuta et al., *Biosynthetic studies on oleandomycin by incorporation of the chemically synthesized aglycones, J. Antibiotics* 43: 909–911, 1990, each of which is incorporated herein by reference).

Figure 2:
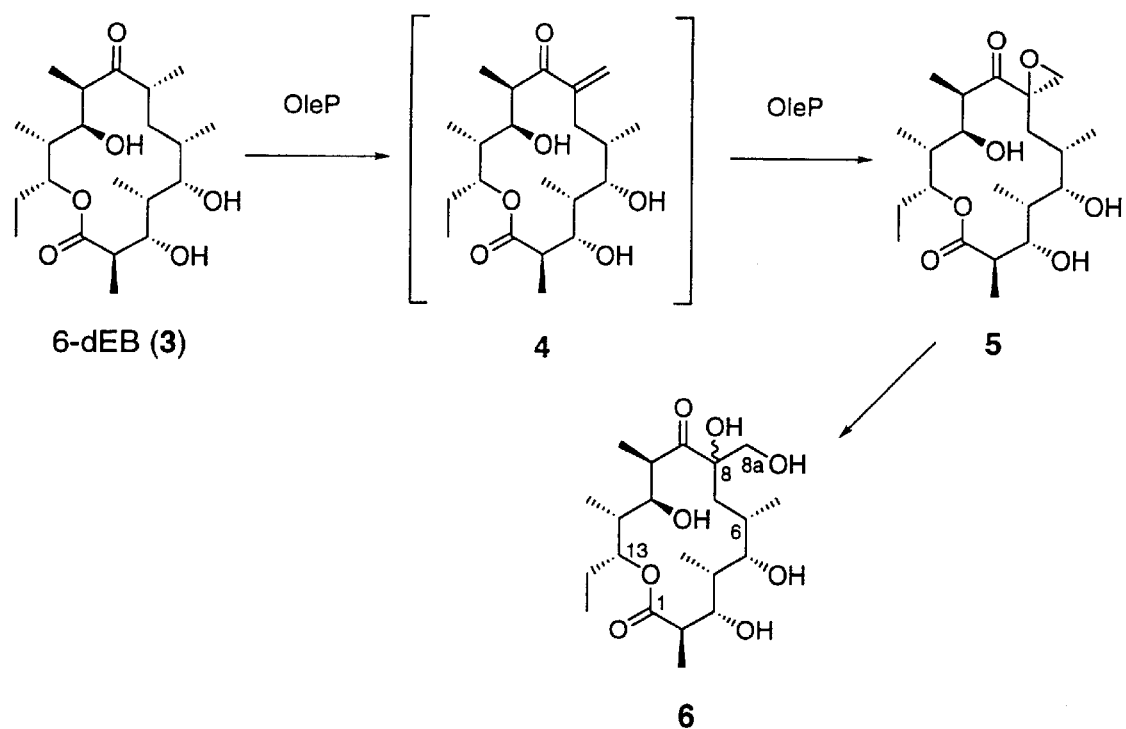
FIG. 2 shows a proposed hydroxylation pathway of 6-dEB by OleP in *S. lividans*. This pathway proceeds through the novel intermediate compound of the invention 8,8a-dehydro-6-deoxyerythronolide B (compound 4). If the OlePKS instead of DEBS were employed, then the compound produced is 8,8a-anhydrooleandolide.

The present invention resolves many of these uncertainties and further provides methods for producing novel polyketides by the heterologous expression of OleP and a PKS such as DEBS or the OlePKS. In one illustrative embodiment, the plasmid pKAO127'kan' (see Ziermann, R. et al., *Recombinant polyketide synthesis in Streptomyces: Engineering of improved host strains, Biotechniques* 26: 106–110, 1999, incorporated herein by reference) a DEBS expression plasmid that produces both 6-dEB (FIG. 2, compound (3)) and 8,8a-deoxyoleandolide (FIG. 1, compound (2)) in *Streptomyces lividans*, was used for coexpression with OleP.

The oleP gene was integrated into the chromosome of *S. lividans* K4-114/pKAO127'kan' using a phiC31-based vector under control of the actll-ORF4 activator and PactI elements. The resulting strain produced a mixture of compounds, of which the predominant components were 8,8a-deoxyoleandolide (compound (2) of FIG. 1) and 6-dEB (~1:7) (compound (3) of FIG. 2). At least six additional compounds were present at levels between 10–50% of 8,8a-deoxyoleandolide, and all appear to be derivatives of 6-dEB, based on MS analysis. Collectively, this amounts to ~33% conversion of the 6-dEB produced by the strain. There were no derivatives of 8,8a-deoxyoleandolide detected, presumably because it was produced in such low quantity compared to 6-dEB in this analysis. However, if the OlePKS were expressed instead of DEBS, then the compounds produced would include 8,8a-dihdroxyoleandolide.

Of the compounds identified, two appeared to be singly hydroxylated species, three appeared to be dehydro derivatives, and one compound appeared to be a dihydroxylated compound when mass spectra were compared to that of 6-dEB. The dihydroxy derivative was selected for structural validation. The structure of this compound 8,8a-dihydroxy-6-deoxyerythonolide B (compound (6) of FIG. 2), was established using mass spectrometry and NMR spectroscopy.

HRFABMS was obtained for the $[M-H_2O+H]^+$ ion ($C_{21}H_{37}O_7$, calculated: 401.2539; observed: 401.2534). DEPT spectra indicated the presence of six methyl, three methylene, nine methine, and three quaternary carbons, consistent with the proposal that a methyl and methine from 6-DEB had been replaced by an oxy-methylene (delta 67.7, C-8a) and oxy-quaternary carbon (delta 91.6, C-8). HMQC NMR data allowed the assignment of two protons resonating at delta 3.45 (d, 11.5 Hz) and 3.60 (d, 11.5 Hz) to C-8a. HMBC correlations between $H_a$-8a and C-8 as well as carbons signals at delta 40.8 (C-7) and 219.1 (C-9) confirmed that the oxidations had occurred at the 8 and 8a positions. Additional NMR data from TOCSY, HMQC, and HMBC (Table 2, below) experiments fully support the assigned structure of 8,8a-dihydroxy-6-deoxyerythonolide B. The absolute stereochemical configuration at C-8 has not been determined.

TABLE 2

$^1$H and $^{13}$C NMR data for 8,8a-dihydroxy-6-deoxyerythonolide B$^a$

| position | $^1$H delta pm (m,J HH) | $^{13}$C delta ppm (m) | HMBC correlations |
|---|---|---|---|
| 1 | | 176.2 (s) | |
| 2 | 2.66 (dq, 10.5, 6.5) | 45.4 (d) | C-1, C-2a, C-3, C-4 |
| 2a | 1.23 (d, 6.5) | 13.7 (q) | C-1, C-2, C-3 |
| 3 | 3.80 (d, 10.5) | 72.9 (d) | C-1, C-2, C-2a, C-4, C-4a, C-5 |
| 4 | 1.93 (m) | 42.8 (d) | C-2, C-4a, C-5 |
| 4a | 1.19 (d, 7.0) | 12.0 (q) | C-5 |
| 5 | 3.50 (ovrlp) | 90.8 (d) | |
| 6 | 1.73 (ovrlp) | 36.5 (d) | |
| 6a | 1.07 (d, 6.0) | 17.6 (q) | C-6, C-7, C-8 |
| 7 | 1.56 (dd, 12.5, 12.5) | 40.8 (t) | C-8 |
|   | 2.57 (dd, 12.5, 7.0) | | C-5 |
| 8 | | 91.6 (s) | |
| 8a | 3.45 (d, 11.5) | 67.7 (t) | C-7, C-8, C-9 |
|    | 3.60 (d, 11.5) | | C-9 |
| 9 | | 219.1 (s) | |
| 10 | 3.50 (ovrlp) | 41.2 (d) | |
| 10a | 0.95 (d, 7.5) | 7.4 (q) | |
| 11 | 3.59 (m) | 69.2 (d) | |
| 12 | 1.71 (m) | 41.6 (d) | |
| 12a | 0.93 (d, 7.5) | 9.0 (q) | C-11, C-12 |
| 13 | 5.36 (ddd, 9.5, 7.0, <1) | 76.2 (d) | C-1, C-11, C-12, C12a, C-14, C15 |
| 14 | 1.51 (m) | 25.7 (t) | |
|    | 1.74 (m) | | |
| 15 | 0.90 (t, 7.5) | 10.4 (q) | C-13, C-14 |

$^a$Recorded in $CDCl_3$

Based on the structure of 8,8a-dihydroxy-6-deoxyerythonolide B, one can conclude that OleP is partly or wholly responsible for introduction of the oleandomycin epoxide and that this step most likely occurs prior to deoxysugar attachment. The presence of the diol could be explained by formation of the epoxide (compound (5) of FIG. 2) and subsequent hydrolysis by an endogenous enzyme in Streptomyces lividans to 8,8a-dihydroxy-6-deoxyerythonolide B. This is further supported by the presence of small amounts of a dehydro derivative (putatively at carbons C-8,8a) compound (compound (4) of FIG. 2) in the mixture. An alternative explanation is that an additional enzyme(s) present in *S. antibioticus* is required for formation of the epoxide, and in its absence, OleP performs the double hydroxylation. In either case, this result suggests that epoxide formation occurs prior to attachment of the two sugars, which was heretofore unknown.

The following examples are given for the purpose of illustrating the present invention and shall not be construed as being a limitation on the scope of the invention or claims.

EXAMPLE 1

Bacterial Strains and Culture Conditions

DNA manipulations were performed in *Escherichia coli* XL1-Blue (Stratagene) and DH10B (BRL). *Streptomyces lividans* K4-114 and K4-155, genotypically identical strains which contain deletions of the entire actinorhodin gene cluster, were used as host strains for the production of polyketide compounds (see Ziermann et al., *Recombinant polyketide synthesis in Streptomyces: Engineering of improved host strains, Biotechniques* 26: 106–110, 1999, and U.S. patent application Ser. No. 09/181,833, filed Oct. 28, 1998, each of which is incorporated herein by reference). *S. lividans* was transformed according to standard methods, and clones were selected with thiostrepton (50 μg/ml) or apramycin (200 μg/ml) overlays on R5 regeneration plates (see Hopwood et al., *Genetic Manipulation of Streptomyces: A Laboratory Manual, The John Innes Foundation*, Norwich, U.K., 1985, incorporated herein by reference).

EXAMPLE 2

Cloning of the Oleandomycin Biosynthesis Gene Cluster from *Streptomyces antibioticus*

Genomic DNA was isolated from an oleandomycin producing strain of *S. antiobioticus* (ATCC 11891) using standard procedures (see Hopwood et al., supra). A genomic library was prepared in Supercos™ (Stratagene) using DNA partially digested with Sau3A I following the supplier's protocols. A probe was prepared by PCR amplification of genomic DNA using primers specific to the KS domains of modules 5 and 6 of OlePKS. The genomic library was then probed by colony hybridization with $^{32}$P-labeled probe. Cosmids containing the desired DNA inserts were verified by PCR with the same primers and by comparison of restriction digest patterns to known sequences. Two overlapping cosmids, pKOS055-5 and pKOS055-1, were identified which cover approximately 65 kb of DNA and contain the entire oleandomycin gene cluster. See PCT publication No. 00/026349 and U.S. patent application Ser. No. 09/428, 517, filed Oct. 28, 1999, each of which is incorporated herein by reference.

EXAMPLE 3

DNA Sequencing and Analysis

Six fragments ~5 kb in size and containing the desired region of the PKS to be sequenced were subcloned from cosmid pKOS055-5. Shotgun libraries were made from each subclone using HinP1 I partially digested DNA cloned into pUC19. Insert sizes ranged from 500–3000 bp. PCR-based double-stranded DNA sequencing was performed on the shotgun clones using a Beckman CEQ 2000 capillary sequencer. Modules 1–4 of the PKS gene cluster were sequenced to approximately 4x coverage. Sequence was assembled using the Sequencher™ (Gene Codes Corp.) software package and analyzed with MacVector (Oxford Molecular).

EXAMPLE 4

Construction of Expression Plasmids for OlePKS and OleP

The OlePKS expression plasmid pKOS098-4 was constructed by replacing the eryAI-AIII genes between the Nde I and EcoRI sites of pKAO127'kan' (Ziermann et al., supra) with the oleAl-AIII genes. A 15.2-kb Nsi I-EcoR I fragment containing oleAl and a portion of oleAII from cosmid pKOS055-5 was subcloned into a vector containing an Nde I site 3 nucleotides (nt) from the 5' terminus of the Nsi I site to generate pKOS039-116. The 15.2-kb Nde I-EcoR I fragment was then subcloned into another vector containing a PacI site 15 nt from the 5' terminus of the Nde I site resulting in pKOS039-110. This generated the following sequence upstream of the Nsi I site in OleAI (Pac I and Nsi I sites are underlined, Nde I site is in bold): 5'-TTAATTAAGGAGGACCATATGCAT-3'. The 15.2 kb Pac I-EcoR I fragment from pKOS039-110 was then cloned into the corresponding sites of pKAO127'kan' to yield pKOS038-174.

Next, a 14-kb EcoRI-EcoRV fragment and a 5.4-kb EcoRV-Pst I fragment, together containing the remaining portions of the oleAII and oleAIII genes, were obtained from cosmid pKOS055-1 and cloned concomitantly into pLitmus28 (Stratagene) to give pKOS039-115. A 20-kb SpeI-Xba I encompassing both of the former fragments was then excised and subcloned into another vector to introduce an EcoRI cloning site downstream of the oleAIII gene. This allowed a 20-kb EcoRI fragment to be extracted from this plasmid and inserted into the EcoR I site of pKOS038-174 (see above) to complete construction of the OlePKS expression vector pKOS0984.

The oleP gene was PCR amplified using the following oligonucleotide primers (forward, 5'-TTTCATATGGTGACCGATACGCACACCGGA-3', reverse, 5'-TTTGAATTCTCACCAGGAGACGATCTGGCG-3'). After subcloning in PCRScript (Stratagene), the Nde I-EcoRI fragment containing oleP was isolated and cloned into pSET152-based plasmid pKOS010-153 (see Xue et al., *A multi-plasmid approach to preparing large libraries of polyketides*, Proc. Natl. Acad. Sci. USA 96: 11740–11745, 1999, incorporated herein by reference) replacing the Nde I-EcoR I eryAIII gene fragment to yield pKOS024-83.

EXAMPLE 5

Production and Analysis of Polyketide Analogs

*Streptomyces lividans* transformants were cultured in 5 ml of liquid R5 medium (see Hopwood et al., supra) at 30° C. for 7 days under the appropriate antibiotic selection (thiostrepton 6 μg/ml, apramycin 50 μg/ml). Samples of fermentation broth were analyzed as previously described by LC/MS on a reverse-phase C-18 column (4.6×150 mm) using a Perkin-Elmer SCIEX API100 mass spectrometer. The polyketides were identified by correspondence of their mass spectrum to the products expected or to known standards. Compound 8,8a-dihydroxy-6-deoxyerythonolide B was purified by silica gel chromatography using ethyl acetate/hexane (1:1). Fractions were analyzed by mass spectrometry and those containing the desired compound were pooled together. The structure of 8,8a-dihydroxy-6-deoxyerythonolide B was determined by NMR and mass spectroscopy (details in Table 2, above).

The invention having now been described by way of written description and examples, those of skill in the art will recognize that the invention can be practiced in a variety of embodiments and that the foregoing description and examples are for purposes of illustration and not limitation of the following claims.

We claim:

1. A compound selected from the group consisting of 8-hydroxy-6-deoxyerythronolide B, 8a-hydroxy-6-deoxyerythronolide B, 8-hydroxy-8,8a-deoxyoleandolide, 8a-hydroxy-8,8a-deoxyoleandolide, 8,8a-dihdroxy-6-deoxyerythronolide B, 8,8a-dehydro-6-deoxyerythronolide B, and 8,8a-anhydrooleandolide.

2. The compound of claim 1 that is 8,8a-dihdroxy-6-deoxyerythronloide B.

3. The compound of claim 2 in substantially pure form.

4. The compound of claim 1 that is 8-hydroxy-6-deoxyerythronolide B.

5. The compound of claim 4 in substantially pure form.

6. The compound of claim 1 that is 8a-hydroxy-6-deoxyerythronolide B.

7. The compound of claim 6 in substantially pure form.

8. The compound of claim 1 that is 8-hydroxy-8,8a-deoxyoleandolide B.

9. The compound of claim 8 in substantially pure form.

10. The compound of claim 1 that is 8a-hydroxy-8,8a-deoxyoleandolide B.

11. The compound of claim 10 in substantially pure form.

12. The compound of claim 1 that is 8,8a-dihydro-6-deoxyerythronolide B.

13. The compound of claim 12 in substantially pure form.

14. The compound of claim 1 that is 8,8a-anhydrooleandolide.

15. The compound of claim 14 in substantially pure form.

* * * * *